United States Patent [19]

Petit et al.

[11] Patent Number: 5,073,672
[45] Date of Patent: Dec. 17, 1991

[54] CATALYST OF THE GALLOSILICATE TYPE AND ITS UTILIZATION FOR THE AROMATIZATION OF LIGHT $C_2$–$C_4$ GASES

[75] Inventors: Laurent Petit, Paris; Jean-Paul Bournonville, Cergy Pontoise; Jean-Louis Guth, Mulhouse; Francis Raatz, Acheres; Alain Seive, Mulhouse, all of France

[73] Assignee: Institut Francais Du Petrole, Rueil Malaison, France

[21] Appl. No.: 669,245

[22] Filed: Mar. 14, 1991

Related U.S. Application Data

[62] Division of Ser. No. 379,469, Jul. 12, 1989, Pat. No. 5,010,048.

[30] Foreign Application Priority Data

Jul. 12, 1988 [FR] France ................................. 88 09631

[51] Int. Cl.$^5$ ............................................. C07C 15/00
[52] U.S. Cl. ..................................... 585/415; 585/417
[58] Field of Search ................................ 585/415, 417

[56] References Cited

U.S. PATENT DOCUMENTS 4,808,763  2/1989  Shum .................................... 585/415

Primary Examiner—Curtis R. Davis
Attorney, Agent, or Firm—Millen, White & Zelano

[57] ABSTRACT

A MFI-based gallosilicate type catalyst is described.

The catalyst is characterized by the following composition expressed by weight:
  a) 0.1 to 99.49% of a matrix,
  b) 0.5 to 99.99% of a zeolite having the following approximate chemical formula:

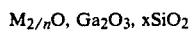

$M_{2/n}O$, $Ga_2O_3$, $xSiO_2$ wherein
M represents a proton and/or a metallic cation,
n is the valence of said cation,
x is a number ranging from 12 to 1,00,
the zeolite of MFI structure synthesized in a fluoride medium having a fluorine content ranging from 0.02 to 1.5% by weight incorporated during synthesis.

The catalyst is notably used in aromatization reactions of light $C_2$–$C_4$ gases in the presence or not of olefins.

8 Claims, No Drawings

CATALYST OF THE GALLOSILICATE TYPE AND ITS UTILIZATION FOR THE AROMATIZATION OF LIGHT $C_2$-$C_4$ GASES

This is a division of application Ser. No. 07/379,469 filed July 12, 1989, and now U.S. Pat. No. 5,010,048.

The present invention relates to:

a catalyst based on a matrix and an MFI-type zeolite containing silica, aluminum and gallium synthesized in fluoride medium, and use of these catalysts in the aromatization reactions of light $C_2$-$C_4$ gases optionally in the presence of olefins.

The synthesis in fluoride media of this type of zeolite having an MFI structure has already been described in French patent No. 88/06509 dated May 11, 1988.

This synthesis involves:

a) in a first step, in preparing a reaction medium solution at a pH less than or equal to about 10 comprising water, at least one silicon source, a trivalent gallium source, at least one source of at least one fluoride ion $F^-$ and at least one structuring agent source providing organic cations containing nitrogen. The structuring agent is chosen from di-, trialkylamines and the ammonium cations derived by protonation of said amines, and/or tetraalkylammonium cations, the alkyl groups preferably being n-propyl groups. Said mixture has a composition in terms of molar ratios included within the following ranges:

$Si^{IV}/Ga^{III}$: 2-1000

$F^-/Si^{IV}$: 0.05-3 organic structuring agent/$Si^{IV}$: 0.04-1

$H_2O/Si^{IV}$: 4-400, b) in a second step, heating said reaction medium at a temperature at the very most equal to about 270° C., advantageously between 80° and 220° C. and preferably between 140° and 210° C., for a period of time required to obtain gallosilicate crystals, c) in a third step, calcining said crystals at a temperature greater than 400° C. and preferably ranging from 500° to 600° C. The object of the calcination step is to eliminate the organic or ammonium cations contained in the crude synthesis solid.

The preferred composition of the starting reaction medium chosen, in aqueous solution, is characterized by molar ratios included within the following ranges:

$Si^{IV}/Ga^{III}$: 8-1000

$F^-/Si^{IV}$: 0.2-2 organic structuring agentt/$Si^{IV}$: 0.06-0.75

$H_2O/Si^{IV}$: 6-200.

The sources of the element $Si^{IV}$ used in the formation of the reaction medium are, for example:

silicas in the form of hydrogels, aerogels, colloidal suspensions, silicas resulting from the precipitation of solutions of soluble silicates, or from the hydrolysis of silicic esters such as the tetraethyl ester of monoorthosilicic acid $Si(OC_2H_5)_4$, or from complexes such as sodium fluorosilicate $Na_2SiF_6$ or ammonium fluorosilicate $(NH_4)_2SiF_6$, silicas prepared by extraction or activation processes of natural or synthetic crystallized compounds.

The sources of the element $Ga^{III}$ used are, for example:

gallium salts (sulfate, nitrate, chloride, fluoride. acetate, for example)

gallium hydroxides, hydroxyoxides and oxides, gallates and various esters.

It is also possible to use sources containing the associated elements silica and gallium such as, for example, glasses or co-gels.

The sources of silica and gallium elements can be used in pulverulent fluid or solid form, as well as in the form of aggregates such as, for example, pellets or extrudates, which can be transformed into zeolites without modification of their shape.

The organic structuring agents used are, for example:

dialkylamines and trialkylamines which will then be transformed in situ into cations during adjustment of the pH to a value below 10, tetraalkylammonium cations added in the form of their salts such as, for example, tetrapropylammonium bromide.

The alkyl groups are preferably n-propyl groups.

The fluoride ions are added in the form of hydrofluoric acid or mineral or organic fluorides such as, for example, sodium fluoride, ammonium fluoride $NH_4F$, ammonium difluoride $NH_4HF_2$, tetrapropylammonium fluoride $(C_3H_7)_4NF$, or hydrolyzable compounds able to release at least one fluoride ion in water, such as, for example, $SiF_4$ or $Na_2SiF_6$, hydrofluoric acid, ammonium fluoride or ammonium bifluoride are the preferred products as they are fairly light and allow protonated gallosilicate type zeolites to be obtained by straightforward calcination of the zeolite resulting from synthesis.

The pH of the reaction medium is less than about 10, advantageously ranging from 2 to 10 and most preferably from 4 to 8. It can be obtained either directly from one or more of the products making up the reaction medium or by addition to said medium of an acid, a base, an acid salt, a basic salt or a complementary buffer mixture.

The addition of crystals (germs) to the reaction medium and stirring generally facilitates the crystallization and also influences the size of the zeolite crystals formed.

Heating of the reaction mixture is preferably carried out in an autoclave internally coated with polytetrafluoroethylene (PTFE). Depending on the composition, the addition of germs, the temperature and stirring is performed, the duration of heating generally ranges from 6 to 650 hours. When crystallization is achieved, the solid obtained is filtered and washed with deionized water.

The gallosilicate zeolites obtained by the process according to the invention are conveniently identified by their X-ray diffraction spectrum. This can be obtained with a diffractometer using the powder-method with K alpha copper rays. The characteristic reticular contour intervals $d_{nkl}$ of the sample are calculated by Bragg's relation from the position of the diffraction peaks, represented by the angle 2 theta. Estimation of the error in $d_{nkl}$ measurement is calculated as a function of the 2 theta absolute error assigned to measurement of 2 theta by Bragg's relation. The currently permitted 2 theta absolute error is equal to ±0.2°. The relative intensity I/Io, I being the intensity of a given line and Io the intensity of the strongest line, assigned to each $d_{nkl}$ value is estimated from the height of the corresponding diffraction peak. Tables 1 and 2 hereinafter represent the X-ray diffraction diagrams of two gallosilicate A- and B-type zeolites obtained according to the process of the present invention, calcined at 550° C. under air, the $Si^{IV}/Ga^{III}$ molar ratio of A is at most equal to 50 and the $Si^{IV}/Ga^{III}$ molar ratio of A is at least equal to 50. The $d_{nkl}$ columns in tables 1 and 2 represent the extreme values the different $d_{nkl}$ equidistances can have. The values depend on the $Si^{IV}/Ga^{III}$ ratio and on the kind of compensation cations, each value indicated in the tables should again be assigned the error in measurement $d_{nkl}$. In order to characterize the relative intensities I/Io, a scale of symbols is often used: FF=very strong, F=strong, mF=medium to strong, m=medium, mf=medium to weak, f=weak, ff=very weak. These relative intensities also partly depend on the gallosilicate-type zeolites obtained.

The solids obtained by the synthesis procedure described hereinabove are zeolites having an MFI structure which have the following approximate chemical formula after calcination, expressed in the oxide form:

$$M_{2/n}O, Ga_2O_3, xSiO_2$$

wherein x can range from 12 to 1,000 and wherein M represents the compensation cation(s) of valence n. The important point is that these solids contain, after the synthesis step as well as after the elimination of organic compounds step, the element fluorine. Fluorine content in the zeolite determined by elemental analysis ranges, for calcined solids, i.e., those resulting from step (c) described hereinabove, from 0.02 to 1.5% by weight, advantageously from 0.05 to 1.0% and preferably from 0.2 to 0.8%.

TABLE 1

X-RAY DIFFRACTION DIAGRAM OF CALCINED GALLOSILICATES B HAVING A MONOCLINICAL STRUCTURE ACCORDING TO THE INVENTION
(measurements of dhkl were stopped at values on the order of 2.97 A, it is nonetheless possible to carry out measurements of dhkl for higher 2 theta values)

| dhkl Å ($10^{-10}$ m) | I/Io | dhkl Å ($10^{-10}$ m) | I/Io |
|---|---|---|---|
| 11.00–11.15 | FF | 4.22–4.27 | f |
| 9.99–9.86 | F | 4.04–4.09 | ff |
| 9.67–9.79 | m | 3.97–4.02 | ff |
| 8.89–9.00 | fff | 3.90–3.95 | fff |
| 7.95–8.06 | fff | 3.82–3.87 | F |
| 7.35–7.44 | fff | 3.79–3.84 | mF |
| 6.99–7.09 | fff | 3.77–3.82 | mF |
| 6.62–6.71 | f | 3.72–3.77 | m |
| 6.29–6.37 | f | 3.70–3.75 | m |
| 5.92–6.00 | mf | 3.69–3.73 | m |
| 5.85–5.93 | f | 3.63–3.6 | ff |
| 5.67–5.74 | f | 3.60–3.65 | ff |
| 5.63–5.70 | f | 3.42–3.46 | fff |
| 5.52–5.59 | f | 3.32–3.37 | fff |
| 5.32–5.39 | ff | 3.28–3.32 | ff |
| 5.09–5.15 | fff | 3.23–3.27 | fff |
| 4.98–5.04 | f | 3.03–3.07 | ff |
| 4.93–4.99 | f | 3.01–3.05 | ff |
| 4.57–4.63 | ff | 2.96–3.00 | f |
| 4.32–4.38 | ff | 2.93–2.97 | ff |

TABLE 2

X-RAY DIFFRACTION DIAGRAM OF CALCINED GALLOSILICATES A HAVING AN ORTHORHOMBIC STRUCTURE ACCORDING TO THE INVENTION

| dhkl ($10^{-10}$ m) Å | I/Io | dhkl ($10^{-10}$ m) Å | I/Io |
|---|---|---|---|
| 11.03–11.18 | FF | 4.32–4.38 | ff |
| 9.90–10.03 | F | 4.22–4.28 | f |
| 9.65–9.78 | m | 4.05–4.11 | fff |
| 8.88–9.00 | fff | 3.97–4.02 | ff |
| 7.93–8.03 | fff | 3.82–3.87 | F |
| 7.36–7.45 | fff | 3.78–3.83 | mF |
| 6.99–7.09 | fff | 3.72–3.77 | m |
| 6.63–6.72 | ff | 3.69–3.74 | m |
| 6.30–6.38 | f | 3.62–3.67 | m |
| 5.93–6.01 | mf | 5.56–3.61 | fff |
| 5.89–5.97 | f | 3.41–3.45 | ff |
| 5.65–5.72 | f | 3.32–3.37 | ff |
| 5.52–5.59 | f | 3.29–3.33 | ff |
| 5.32–5.39 | ff | 3.23–3.27 | fff |
| 5.07–5.14 | fff | 3.03–3.07 | ff |
| 4.97–5.04 | ff | 2.96–3.00 | f |
| 4.93–4.99 | ff | 2.94–2.97 | ff |
| 4.57–4.63 | ff | | |

Measurements of $d_{nkl}$ were stopped at values in the order of 2.97 A, it is nonetheless possible to carry out measurements of $d_{nkl}$ for higher 2 theta values.

The galloslicate-type zeolites of the invention have acid properties that are completely different from those of zeolites having a conventional MFI structure obtained in an alkaline medium [U.S. Pat. No. 3,702,886 (1972); Ger. Offen. 2,755,770 (1974); U.S. Pat. No. 4,554,146 (1985); JP 190818 (1983) and JP 64813 (1983)].

The characteristic acidity of the solids resulting from the introduction of fluorine during synthesis is taken advantage of to prepare catalysts likely, for example, to aromatize a hydrocarbon such as propane and, more generally, a $C_2$–$C_4$ light-gas cut in the optional presence of olefins and whose acid properties are of a new kind.

The present invention thus relates to a gallosilicate-type catalyst characterized by the following composition expressed by weight:

a) 0.1 to 99.49% of a matrix chosen from the group formed by alumina, silica, magnesia, a clay and any combination of at least two of the compounds mentioned hereinabove and c) 0.51 to 99.99% of a zeolite synthesized in a fluorine medium having the following approximate chemical formula:

$$M_{2/n}O, Ga_2O_3, xSiO_2$$

wherein

M represents a proton and/or a metallic cation,
n is the valence of the cation,
x is a number ranging from 12 to 1000,
the zeolite having a fluorine content ranging from 0.02 to 1.5% by weight, preferably from 0.1 to 1% by weight, the fluorine being incorporated during synthesis, said zeolite also being characterized by the X-ray diffraction diagram given in Table I or II.

In a more detailed manner, after synthesis in a fluorine medium, the solid can, if need be, be subjected to a defluorination process, allowing its acid properties to be adjusted.

The synthesized zeolite containing fluorine and of a gallosilicate type having an MFI structure is characterized by:

a fluorine content ranging from 0.02 to 1.5% by weight, a $Si^{IV}/Ga^{III}$ molar ratio at least equal to 8.6, an X-ray diffraction diagram chosen from the group comprised of the diagram in Table I having a monoclinical structure and the diagram in Table II having an orthorhombic structure.

The zeolite according to the invention preferably has an infrared spectrum which has Si—OH bands (around 3740 cm$^{-1}$) and GaOH bands (around 3620 cm$^{-1}$) that are less intense than the gallosilicates of the prior art having the same Si/Ga ratio.

Defluorination treatment is more or less severe depending on the level of defluorination desired. It consists of one or more successive treatments of the solid under reflux in an ammonium hydroxide solution having a normality ranging from 0.05 to 5N and preferably from 0.1 to 3N, for a period of time ranging from about 0.5 to 5 hours and preferably from 1 to 4 hours with a v/w ratio, defined as the volume of solution to dry solid weight, ranging from about 5 to 50 cm$^3$g$^{-1}$ and preferably from 10 to 30 cm$^3$g$^{-1}$. The solid, after each washing, is then abundantly washed with distilled water and dried in the oven. After these treatments and depending on their severity, the fluorine content of the solid ranges from 0.9 to 0.01% by weight. If practically all the fluorine is eliminated by repeated treatment, solids are again obtained which are distinguished, in particular, by their IR spectrum in the region of 3800-3500 cm$^{-1}$ of zeolites having a conventional MFI structure with the same Si/Al ratio of the framework: the solids contained in the catalyst according to the invention have a larger proportion of Si—OH groups.

The partially or totally defluorinated solid can be mixed with a generally amorphous matrix, for example, a wet alumina gel powder. The mixture is then shaped, for example, by extrusion through a die.

Zeolite content of the support thus obtained generally ranges from about 0.5 to 99.99% and advantageously from about 40 to 90% by weight. More particularly, it ranges from about 60 to 85% by weight with respect to the zeolite and matrix together.

Matrix content in the catalyst advantageously ranges from about 10 to 60% and preferably from about 15 to 40% by weight. Shaping can be carried out with matrices other than alumina such as for, example, magnesia, silica-alumina, and natural clays (kaolin, bentonite), and by techniques other than extrusion such as pelleting or coating.

The zeolite, partially or totally defluorinated, can, before or after shaping with an amorphous matrix, be treated in the presence of steam at a high temperature. This treatment, already described in the case of synthesized gallosilicates in an alkaline medium (WO 84/03879), advantageously increases the catalytic properties of the solid for the aromatization reaction of a C$_2$-C$_4$ cut. This treatment consists in a calcination carried out under gas (air or gas containing air or an inert gas), this gas preferably containing from 5% to 100% of steam, at a temperature ranging from 400° to 900° C., preferably from 450° to 600° C.

The effect of this treatment together with the presence of fluorine provides the solid with a new kind of acidity, leads to a catalyst with improved performance in the aromatization reaction of light gases in comparison with catalysts of the prior art not containing fluorine.

The catalyst obtained by the procedures described hereinabove is used for the aromatization reaction of light gases, for example, propane and/or a C$_2$-C$_4$ mixture optionally in the presence of olefins. This reaction is of particular interest as it enhances the residues of refining processes (C$_2$-C$_4$) into products of greater value (benzene, toluene, xylenes) while contributing to the production of large amounts of hydrogen required for example, for hydrotreatment processes.

The charge containing butane and/or propane and/or ethane, in the optional presence of olefins, is contacted with the catalyst prepared according to the previous procedures at a temperature ranging from 400° to 700° C., and more particularly, from 500° to 600° C.

The following examples describe the invention without in any way limiting its scope, they are given for a charge uniquely comprised of propane but can be easily adapted to a more complex charge comprised of a mixture of C$_2$-C$_4$ light gases, optionally, in the presence of olefins.

EXAMPLE 1

Preparation of zeolites A and B entering into the composition of the catalyst according to the invention.

Two zeolites having a MFI structure with Si/Al atomic ratios close to 25 and 150 are prepared from the reaction mixtures consisting of:

a silica source of composition SiO$_2$, marketed under the name of Aerosil 130, a gallium source: gallium chloride solution prepared by dissolving metallic gallium in concentrated hydrochloric acid, the GaIII concentration of this solution is 0.72 mole/l, ammonium fluoride, tetrapropylammonium bromide (TPA Br), crystallization germs (ground zeosilite or gallozeosilite crystals).

The molar compositions of the different reaction mixtures thus prepared, with respect to one mole of silica, are as follows:

1SiO$_2$; xGaCl$_3$; 0.25 TPABr; 0.5 NH$_4$F; 50 H$_2$O wherein x is equal to $5.10^{-2}$ in the case of zeolite A and $10^{-2}$ in the case of zeolite B.

The synthese are carried out in autoclaves internally coated with polytetrafluoroethylene; the autoclaves are maintained at 200° C. for 4 days.

After cooling, the solids obtained are separated from the mother liquors by filtration and washed. The calcined crystals (550° C., 8 hours) of these two samples have X-ray diffraction diagrams analogous to those given in Table 1 in the case of zeolite A and Table 2 in the case of zeolite B. The size of these crystals is about a few micrometers.

The initial and final pHs of the synthesis medium, as well as the principal physiochemical characteristics of the solids obtained, are reported in Table 3 as a function of parameter x, which characterizes the initial reaction medium. The data in this table show that solids A and B contain substantial amounts of fluorine, even after the calcination step at 550° C. under air.

TABLE 3

|  | Zeolite A | Zeolite B |  |
|---|---|---|---|
| x | $5.10^{-2}$ | $10^{-2}$ | (1) |
| initial pH | 2 | 7 |  |
| final pH | 2 | 5 |  |

TABLE 3-continued

|  | Zeolite A | Zeolite B |  |
|---|---|---|---|
| molar ratio | 23.8 | 93.0 |  |
| % wt F⁻ before calcination | 0.62 | 0.88 | (2) |
| % wt F⁻ after calcination at 550° C. under air | 0.3 | 0.2 |  |
| result of XD diagrams | orthorhombic (table 1) | monoclinical (table 2) |  |

(1) characteristics of the reaction mixture
(2) characteristics of the MFI-structure gallosilicates obtained

EXAMPLE 2

Catalysts A1 and B1 conform with the invention.

Zeolites A and B of Example 1 are shaped by extrusion with an alumina-type binding agent in a proportion of 20% by weight of binding agent per 80% by weight of zeolite. The solids obtained respectively designated A1 and B1 are calcined at 600° C. for 2 hours.

These two catalysts are tested for aromatization of propane at 550° C. and under atmospheric pressure. The propane is diluted in argon at a proportion of 20% of $C_3H_8$ per 80% of Ar. The catalytic performance is reported in table 4.

It is defined by:

$PPH$ = hourly mass velocity = hourly mass flow/zeolite mass $$\left(\begin{array}{c}\text{conversion of}\\ \text{propane (\% wt)}\end{array}\right) = \left[\left(\begin{array}{c}\text{weight of}\\ \text{propane}\\ \text{in the charge}\end{array}\right) - \left(\begin{array}{c}\text{weight of}\\ \text{products}\\ \text{recovered}\end{array}\right)\right] / \left(\begin{array}{c}\text{weight of propane}\\ \text{in the charge}\end{array}\right)$$

(selectivity in) one product $Pi$ (% wt) = 100 ×

$$\frac{\text{(weight of } Pi \text{ recovered)}}{\left(\begin{array}{c}\text{weight of propane in}\\ \text{the charge}\end{array}\right) - \left(\begin{array}{c}\text{weight of products}\\ \text{recovered}\end{array}\right)}$$

$$\frac{\text{(yield in one product)}}{(\% \text{ wt})} = \frac{\text{weight of product } Pi \text{ recovered}}{\text{weight of propane in the charge}}$$

EXAMPLE 3

Preparation of defluorinated zeolite A of the present invention, illustrates the importance of fluorine in the catalytic properties for the aromatization of propane.

The zeolite is submitted to 3 cycles:
0.2N NH₄OH solution at 140° C. for 4 hours
filtration and washing with distilled water
drying in the oven at 150° C.

After treatment, a solid is obtained whose crystallinity and Si/Al ratio are unaltered but whose fluorine content is below the limit of detection of our determination method, which is 0.02% F (wt).

The solid thus obtained is shaped according to the conditions of Example 2 and is designated A2. Tested for the aromatization of propane according the conditions described in Example 2, it is observed that the catalytic performance of A2 reported in table 4 is less than those of catalyst A1, from the point of view of both selectivity of aromatic products and catalytic activity in particular.

EXAMPLE 4

This example shows the advantages of a pretreatment at a high temperature in the presence of steam of the catalysts of the present invention for the aromatization of propane.

Catalyst B1 of Example 2 is used as the starting solid. Before the catalytic test on the aromatization of propane, the catalyst is pretreated in situ according to the following procedure:
rate of increase in temperature 10° C./mn
air flow rate 3 l h⁻¹ g⁻¹
injection of water at 400° C. and flow rate of 2.25 cm³ h⁻¹ g⁻¹ of liquid water, i.e. a molar content in steam of 50%;
final temperature 500° C. with a stage of 30 mm at this temperature.

The solid obtained is designated B2.

The catalytic test, the results of which are given in Table 4, shows that the catalytic activity is substantially increased with respect to the starting solid B1 and, more particularly, that selectivity for aromatic products is found to be much greater.

EXAMPLE 5

Comparison catalyst C1.

Zeolite C is a MFI structure zeolite synthesized in conventional basic medium, the description of which is given in U.S. Pat. No. 4,554,146. The solid obtained has a $Si^{IV}/Ga^{III}$ ratio of 62.0 and is completely free of fluorine after synthesis. Shaped and tested for aromatization of propane according to the conditions of Example 2, this catalyst designated C1 is revealed to be both less active and less selective than the catalysts of the present invention. Its catalytic performances are similar to those of catalyst A1 which is obtained from the zeolite according to the present invention but defluorinated.

EXAMPLE 6

Comparison catalyst C2.

Catalyst C1 of Example 5 is pretreated according to the conditions of Example 4. The solid obtained designated C2 is much less active than solid B2 of the present invention pretreated under the same conditions. This example illustrates the influence of fluorine on the acid properties and thus on the activity of catalysts for the aromatization reaction of propane.

EXAMPLE 7

Comparison catalyst C3.

Zeolite C of Example 5 is fluorinated by treatment at 450° C. under an atmosphere containing CHF₃ for 4 hours. The fluorine content achieved at the end of this treatment is 0.15% by weight. This solid is then shaped and tested according to the conditions of Example 2. The catalytic performance of catalyst C3 thus prepared is reported in Table 4. It can be clearly seen that at a fluorine content similar to that of the catalysts of the present invention, the catalysts fluorinated by a modifying treatment after synthesis have poor catalytic performance.

TABLE 4

| CATALYST | A1 | B1 | A2 | B2 | C1 | C2 | C3 |
|---|---|---|---|---|---|---|---|
| Si/Al | 28.8 | 93.0 | 23.8 | 93.6 | 62.0 | 62.0 | 71.3 |
| % F | 0.3 | 0.2 | <0.02% | 0.2 | 0 | 0 | 0.15 |
| PPH | 0.8 | 0.8 | 0.8 | 0.8 | 0.8 | 0.8 | 0.8 |
| Conversion of propane | 83.0 | 45.6 | 70.1 | 62.1 | 45.0 | 51.4 | 12.9 |

TABLE 4-continued

| CATALYST | A1 | B1 | A2 | B2 | C1 | C2 | C3 |
|---|---|---|---|---|---|---|---|
| B, T, X yield | 44.1 | 22.0 | 21.7 | 35.4 | 14.5 | 18.2 | 0.5 |
| B, T, X selectivity | 54.0 | 49.1 | 31.2 | 57.0 | 32.3 | 33.5 | 4.1 |

We claim:

1. A process for the aromatization of a $C_{2-4}$-light-gas cut, comprising subjecting a feed of said cut to aromatization conditions, in the presence of a catalyst comprising by weight:
   (a) 0.01 to 99.49% of a matrix chosen from the group consisting of alumina, silica, magnesia, and a clay; and
   (b) 0.51 to 99.99% of a gallosilicate zeolite synthesized in a fluorine-containing medium having an MFI structure comprising:
      a fluorine content of 0.02 to 1.5% by weight,
      an $Si^{IV}/Ga^{III}$ molar ratio at least equal to 8.6, and
      an X-ray diffraction diagram chosen from the group consisting of the diagram in Table 1 having a monoclinical structure and the diagram in Table 2 having an orthorhombic structure.

2. A process according to claim 1, wherein in the catalyst the fluorine content is 0.05-1% by weight.

3. A process according to claim 1, wherein in the catalyst the fluorine content is 0.2-0.8% by weight.

4. A process according to claim 1, wherein in the catalyst the zeolite content is 40-90% by weight.

5. A process according to claim 1, wherein in the catalyst the zeolite content is 60-85% by weight.

6. A process according to claim 3, wherein in the catalyst the zeolite content is 60-85% by weight.

7. A process according to claim 1, wherein the catalyst is prepared by a process comprising combining, at a pH less than or equal to 10 to form a mixture, water, a source of silicon, a source of gallium, a source of fluorine anions, and at least one structuring agent providing organic cations containing nitrogen; heating said mixture so as to produce gallosilicate crystals; and, optionally, calcining said crystals.

8. A process according to claim 1, wherein in the catalyst the zeolite has an infrared spectrum with Si—OH bands (around 3740 cm$^{-1}$) and GaOH bands (around 3620 cm$^{-1}$) that are less intense than the gallosilicates of the prior art having the same Si/Ga ratio.

* * * * *